(12) United States Patent
Bosma et al.

(10) Patent No.: US 11,575,234 B2
(45) Date of Patent: Feb. 7, 2023

(54) ELECTRICAL CONNECTOR WITH USB SERIES A CONTACT PAD PITCH

(71) Applicant: KONINKLIJKE PHILIPS N.V., Eindhoven (NL)

(72) Inventors: Robert Willem Bosma, Sterksel (NL); Johannes Antonius Van Rooij, Best (NL); Willem-Jan Arend De Wijs, Oss (NL); Jan Harm De Boer, Neunen (NL); Mustafa Hakan Gokgurler, Helmond (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 70 days.

(21) Appl. No.: 17/266,184

(22) PCT Filed: Aug. 8, 2019

(86) PCT No.: PCT/EP2019/071344
§ 371 (c)(1),
(2) Date: Feb. 5, 2021

(87) PCT Pub. No.: WO2020/030751
PCT Pub. Date: Feb. 13, 2020

(65) Prior Publication Data
US 2021/0257793 A1    Aug. 19, 2021

Related U.S. Application Data

(60) Provisional application No. 62/716,122, filed on Aug. 8, 2018.

(30) Foreign Application Priority Data

Oct. 31, 2018   (EP) .................................... 18203605

(51) Int. Cl.
*H01R 24/60* (2011.01)
*H01R 13/516* (2006.01)
(Continued)

(52) U.S. Cl.
CPC ........... *H01R 24/60* (2013.01); *H01R 13/516* (2013.01); *H01R 13/629* (2013.01); *H01R 13/64* (2013.01);
(Continued)

(58) Field of Classification Search
CPC .... H01R 24/60; H01R 13/516; H01R 13/629; H01R 13/64; H01R 13/6598
(Continued)

(56) References Cited

U.S. PATENT DOCUMENTS 7,249,978 B1 *  7/2007  Ni ......................... G06K 19/07
                                                            361/752
7,798,853 B2 *  9/2010  Shi ..................... H01R 13/7195
                                                            439/607.58
(Continued)

FOREIGN PATENT DOCUMENTS

WO    2008110219 A1   9/2008
WO    2012008411 A1   1/2012

OTHER PUBLICATIONS

International Search Report and Written Opinion of PCT/EP2019/071344, dated Oct. 18, 2019.
(Continued)

*Primary Examiner* — Alexander Gilman (57) ABSTRACT

A male connector (100) includes a contact pad substrate (101) and a connector shell (102). The contact pad substrate (101) includes a linear array of contact pads (103a, 103b, 103c, 103d) that are adapted for aligning with corresponding contacts (103'a, 103'b, 103'c, 103'd) of a contact-bearing tongue (104') of a corresponding female connector (100')
(Continued)

that conforms to a USB Series A receptacle contact pad pitch specification. The two outermost contact pads (103a, 103d) of the linear array are electrically connected together. The connector shell (102) is formed from an insulating material and comprises a tubular portion (102a) for insertion into the corresponding female connector (100'), and a handling portion (102b) for handling during insertion.

10 Claims, 7 Drawing Sheets

(51) Int. Cl.
    *H01R 13/629*     (2006.01)
    *H01R 13/64*     (2006.01)
    *H01R 13/6598*     (2011.01)

(52) U.S. Cl.
    CPC ..... *H01R 13/6598* (2013.01); *H01R 2201/12* (2013.01)

(58) Field of Classification Search
    USPC .......................................................... 439/660
    See application file for complete search history.

(56) References Cited

U.S. PATENT DOCUMENTS

| | | | |
|---|---|---|---|
| 7,815,469 B1* | 10/2010 | Nguyen | H01R 13/6658 439/353 |
| 7,872,873 B2* | 1/2011 | Hiew | H01L 24/97 361/737 |
| 8,545,269 B2* | 10/2013 | Ore-Yang | H01R 13/6658 439/620.22 |
| 9,350,125 B2* | 5/2016 | Jones | H01R 24/60 |
| 9,478,918 B1* | 10/2016 | Yin | H01R 13/6315 |
| 9,537,261 B2* | 1/2017 | Chen | H01R 13/642 |
| 9,647,388 B1* | 5/2017 | Ray | H01R 13/6275 |
| 10,014,638 B1* | 7/2018 | McCracken | H01R 24/60 |
| 10,074,947 B2* | 9/2018 | Tsai | H01R 27/00 |
| 2006/0216991 A1* | 9/2006 | Boutros | H01R 13/6582 439/358 |
| 2008/0067248 A1* | 3/2008 | Hiew | G06K 19/07741 235/441 |
| 2008/0160811 A1 | 7/2008 | Dunstan | |
| 2010/0087098 A1* | 4/2010 | Sloey | H01R 13/4538 439/660 |
| 2013/0115821 A1* | 5/2013 | Golko | H01R 13/6582 439/638 |
| 2014/0206209 A1* | 7/2014 | Kamei | H01R 24/60 439/81 |
| 2017/0331235 A1* | 11/2017 | Yokoyama | H01R 12/724 |
| 2019/0267764 A1* | 8/2019 | Wu | H01R 13/502 |
| 2021/0111514 A1* | 4/2021 | Ichikawa | H01R 13/512 |
| 2021/0257793 A1* | 8/2021 | Bosma | H01R 13/6598 |
| 2022/0094102 A1* | 3/2022 | Asano | H01R 13/5227 |
| 2022/0224056 A1* | 7/2022 | Kawasaki | H01R 13/6474 |

OTHER PUBLICATIONS

Compaq Hewlett=Packard "Universal Serial Bus Specification" Revision 2.0. Apr. 2000.

* cited by examiner

Figure 6-9. USB series "A" Plug interface drawing

ELECTRICAL CONNECTOR WITH USB SERIES A CONTACT PAD PITCH

CROSS-REFERENCE TO PRIOR APPLICATIONS

This application is the U.S. National Phase application under 35 U.S.C. § 371 of International Application No. PCT/EP2019/071344, filed on Aug. 8, 2019, which claims the benefit of U.S. Provisional Patent Application Ser. No. 62/716,122, filed Aug. 8, 2018 and European Patent Application No. 18203605.3, filed on Oct. 31, 2018. These applications are hereby incorporated by reference herein.

FIELD OF THE INVENTION

The invention relates to an electrical connector. The electrical connector includes features to reduce the risk of harm to a patient or damage to electrical equipment connected thereto. The invention may be used in various fields. In one exemplary application in the medical field the connector may be connected to a sensor that is disposed on a medical device.

BACKGROUND OF THE INVENTION

A document "Universal Serial Bus Specification" Revision 2.0, Apr. 27, 2000, published by the USB implementers forum (USB-IF) on 23 Mar. 2005 [1] governs, amongst other details, the mechanical form factor of this commonly-used connector type. This document specifies on page 99, FIG. 6-9, a plug having an insertable body having a length exceeding 11.75 millimeters, a width of 12.00±0.1 millimeters, and a height of 4.5±0.1 millimeters. A contact pad substrate is also specified on page 99, FIG. 6-9 of this document in which a linear array of four contact pads includes two outermost contact pads and two innermost contact pads. The two innermost contact pads have a pitch of 2.00±0.05 millimeters, and the pitch between each innermost contact pad and its nearest outermost contact pad is 2.5±0.05 millimeters. A contact-bearing tongue of the corresponding female connector that conforms to a USB Series A receptacle contact pad pitch specification is also specified in this document on P.115 in FIG. 6-12, and this has the same pitch specification as the plug. The insertable body of the plug surrounds the contact pad substrate and is conventionally formed from a conductor in order to electrically shield the contacts from electromagnetic interference, i.e. EMI, and to provide an electrical connection between this shield and the shield of the receptacle. The aforementioned document also specifies that the insertable body includes an overmolded boot having a maximum width of 16.0 millimeters and a maximum height of 8.0 millimeters.

In spite of the numerous advantages of the aforementioned USB series A plug, there remains room to provide an improved electrical connector.

SUMMARY OF THE INVENTION

The present invention seeks to provide an improved electrical connector. The electrical connector includes a contact pad substrate that conforms to the USB Series A plug contact pad pitch specification in order to reduce substrate cost, and is altered in other aspects.

The invention is defined by the claims.

Thereto, a male connector for mating with a corresponding female connector by applying pressure along an insertion axis is provided. The male connector includes a contact pad substrate and a connector shell. The contact pad substrate includes a linear array of contact pads including two outermost contact pads and two innermost contact pads. The two outermost contact pads are electrically connected together. The two innermost contact pads have a pitch of 2.0 millimeters and the pitch between each innermost contact pad and its nearest outermost contact pad is 2.5 millimeters for aligning with corresponding contacts of a contact-bearing tongue of the corresponding female connector that conforms to a USB Series A receptacle contact pad pitch specification, specifically that of USB 2. The connector shell is formed from an insulating material and comprises a tubular portion for insertion into the corresponding female connector, and a handling portion for handling during insertion. The tubular portion includes an end face having an opening that defines an entrance to a cavity, which cavity extends along the insertion axis for receiving within the tubular portion the contact-bearing tongue of the corresponding female connector. The contact pad substrate is disposed within the cavity such that the contact pads of the linear array are distributed transversely with respect to the end face, and such that the contact pads are exposed within the cavity for making electrical contact with the corresponding contacts of the contact-bearing tongue of the female connector when the male connector is mated with the female connector.

The male connector is contemplated for use in the vicinity of electrical equipment such as a computer or a tablet in which electrical connectors such as USB Series A receptacles are available, specifically those of USB 2, and also those of a contact pad pitch-compatible USB 3. However, the male connector is contemplated for use in applications in which the power supply of a conventional USB 2 connector, and likewise that of a pitch-compatible USB 3 connector, i.e. the nominal +5 Volts and 0 Volts that is conventionally applied across the two outermost contact pads, is not required. Thus, in the male connector the two outermost contact pads are electrically connected together. This ensures that, despite the male connector's contact pad pitch specification conforming to that of the USB Series A receptacle contact pad pitch specification, and likewise that of a pitch-compatible USB 3, even if the contact pad substrate were inserted into such receptacles, no potential difference can be applied between these contact pads. In the contemplated medical applications in which the male connector may be used, applying even moderate external potential differences such as this to e.g. parts of a patient's nervous system, can have harmful effects.

Moreover, the tubular portion of the connector shell that is adapted for insertion into the corresponding female connector is formed from an insulating material. Conventionally, the corresponding insertable body of a USB 2 Series A plug is formed from a conductor in order to electrically shield the contacts disposed therein from EMI. This conductor also serves to make electrical contact with the corresponding electrical shield of a USB 2 Series A receptacle. As mentioned above, the male connector is contemplated for use in the vicinity of electrical equipment such as a computer or a tablet in which other electrical connectors such as USB Series A receptacles are available. However, in particular when such electrical equipment is un-grounded, the electrical shield of this receptacle can float to a high voltage of many tens of volts or more above ground potential. By forming the tubular portion of the connector shell that is adapted for insertion into the corresponding female connector from an insulating material, it is therefore ensured that even if the end face of the tubular portion were temporarily touched onto the electrical shield of a USB 2 Series A receptacle, and likewise that of a pitch-compatible USB 3 Series A receptacle, the floating potential of the electrical equipment cannot be applied to a patient. Thus, in combination with the feature of electrically shorting together the two outermost contact pads together, this feature further reduces the risk of applying a harmful potential to a patient through mis-insertion of the male connector into known female connectors such as a USB Series A receptacle that may have a similar appearance.

In accordance with one aspect the tubular portion of the male connector includes an insertion key that extends along the insertion axis and outwards with respect to the cavity for preventing insertion of the tubular portion into a USB Series A receptacle. Whilst forming the tubular portion of the connector shell that is adapted for insertion into the corresponding female connector from an insulating material reduces the risk of applying a harmful potential to a patient due to even touching the tubular portion onto an incorrect female connector, the insertion key further reduces this risk by preventing the actual insertion of the male connector into a USB Series A receptacle. Moreover, in combination with the feature of electrically shorting together the two outermost contact pads together, the insertion key has the synergistic effect of preventing damage to the electrical equipment that might otherwise result from the mis-insertion of the male connector into a USB Series A receptacle.

In accordance with one aspect i) a maximum width of the end face of the tubular portion parallel to the linear array is greater than 12.1 millimeters and/or ii) a maximum height of the end face of the tubular portion perpendicular to the linear array is greater than 4.6 millimeters. These features both act to prevent insertion of the tubular portion into a USB Series A receptacle, and consequently further reduce the risk of applying potentially harmful voltages to a patient. The specified dimensions lie outside those of a USB Series A plug, which prescribes an insertable body having a maximum width of 12.00±0.1 millimeters, and a maximum height of 4.5±0.1 millimeters.

In accordance with one aspect the handling portion of the connector shell includes a tapered region having a taper thickness perpendicular to the linear array. The taper thickness increases towards the tubular portion in order to prevent a finger of a user from slipping towards the tubular portion during mating of the male connector with the corresponding female connector. In the contemplated medical applications in which the male connector may be used, sterility is a key requirement. Whilst the male connector, together with any medical device connected thereto, is typically sterilized and packaged before use in order to maintain that sterility, a console to which the male connector is connected by way of a corresponding female connector, may be sterilized less often. The tapered region reduces the risk that the sterile finger of a user that handles the male connector slips and contacts the less-sterile console, subsequently transferring any harmful substances thereon to a patient by way of the user's finger.

In accordance with one aspect the male connector is provided with a sensor and an electrical cable. The sensor includes a first electrical contact and a second electrical contact. The electrical cable includes a first signal conductor, a second signal conductor and an electrical shield configured to electrically shield the first signal conductor and the second signal conductor. The first electrical contact of the sensor is electrically connected to one of the two innermost contact pads of the male connector by the first signal conductor, and the second electrical contact of the sensor is electrically connected to the other of the two innermost contact pads of the male connector by the second signal conductor. Moreover, the electrical shield is electrically connected to both of the two outermost contact pads of the contact pad substrate. In so doing, a single electrical shield may shield both signal conductors. The use of only three electrical conductors, including the shield, in the electrical cable improves its flexibility thereby making it easier to deploy the sensor. In known USB male connectors up to five electrical conductors, including the shield, are used in such an electrical cable: two for electrical signals, two for the nominal +5 Volts and 0 Volts power supply, and one for the electrical shield.

Further aspects are described with reference to the appended claims. Further advantages from the described invention will also be apparent to the skilled person.

DETAILED DESCRIPTION OF THE INVENTION

In order to illustrate the principles of the present invention a male connector is described with particular reference to a medical application in which a sensor is electrically connected to the connector. It is however to be appreciated that the male connector also finds application beyond the medical field, and may be used in the electrical device field in general.

Figure 1:
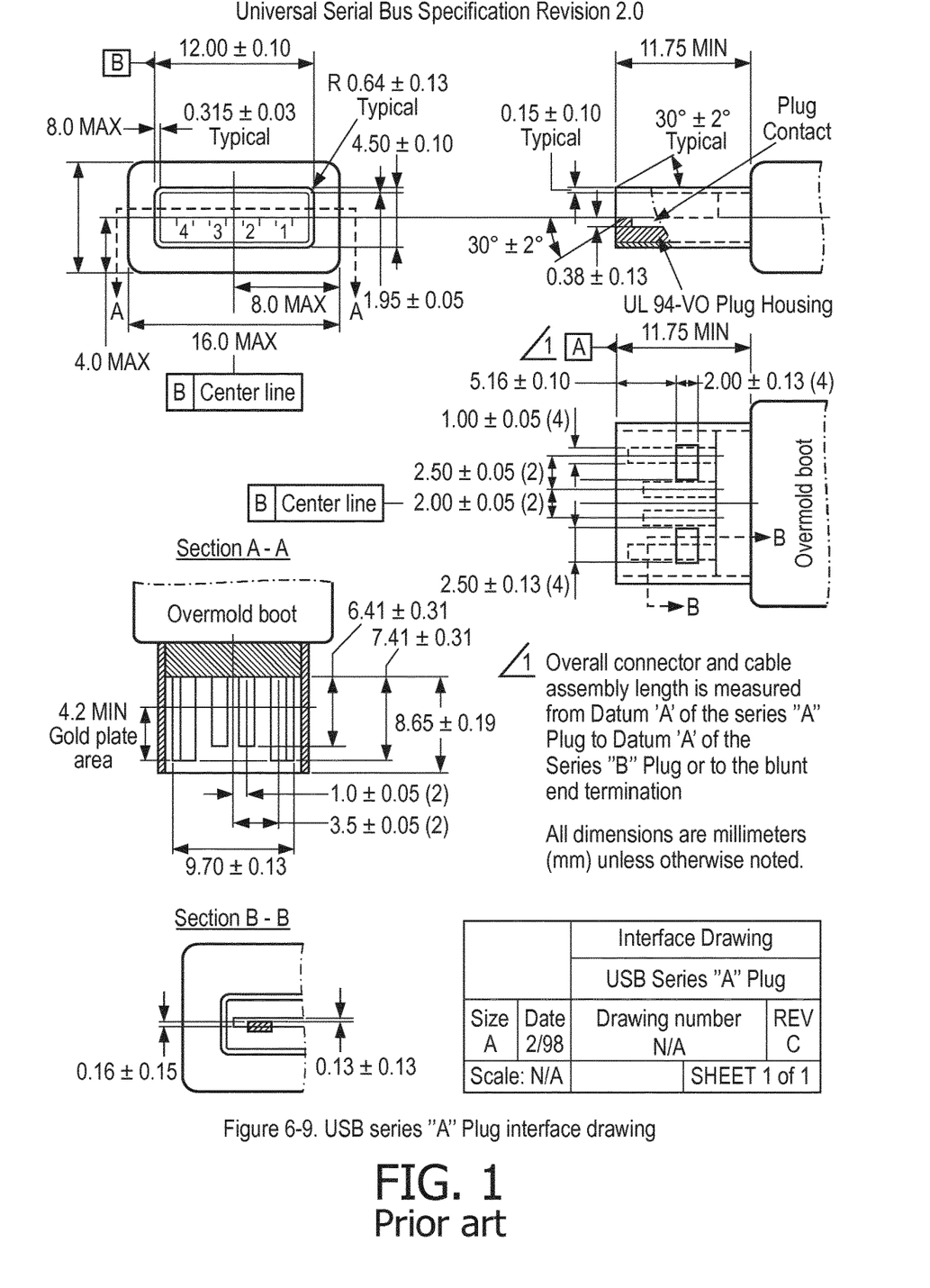
FIG. 1 illustrates a prior art USB Series A Plug according to Revision 2.0.

FIG. 1 illustrates a prior art USB Series A Plug according to Revision 2.0. This section of the full USB 2.0 specification from document [1] describes the mechanical properties of connectors conforming to this specification. In particular it is noted that the contact pad substrate in FIG. 1 along section A-A' includes a linear array of four contact pads having two outermost contact pads and two innermost contact pads. The two innermost contact pads have a pitch of 2.00±0.05 millimeters, and the pitch between each innermost contact pad and its nearest outermost contact pad is 2.5±0.05 millimeters.

Figure 2:
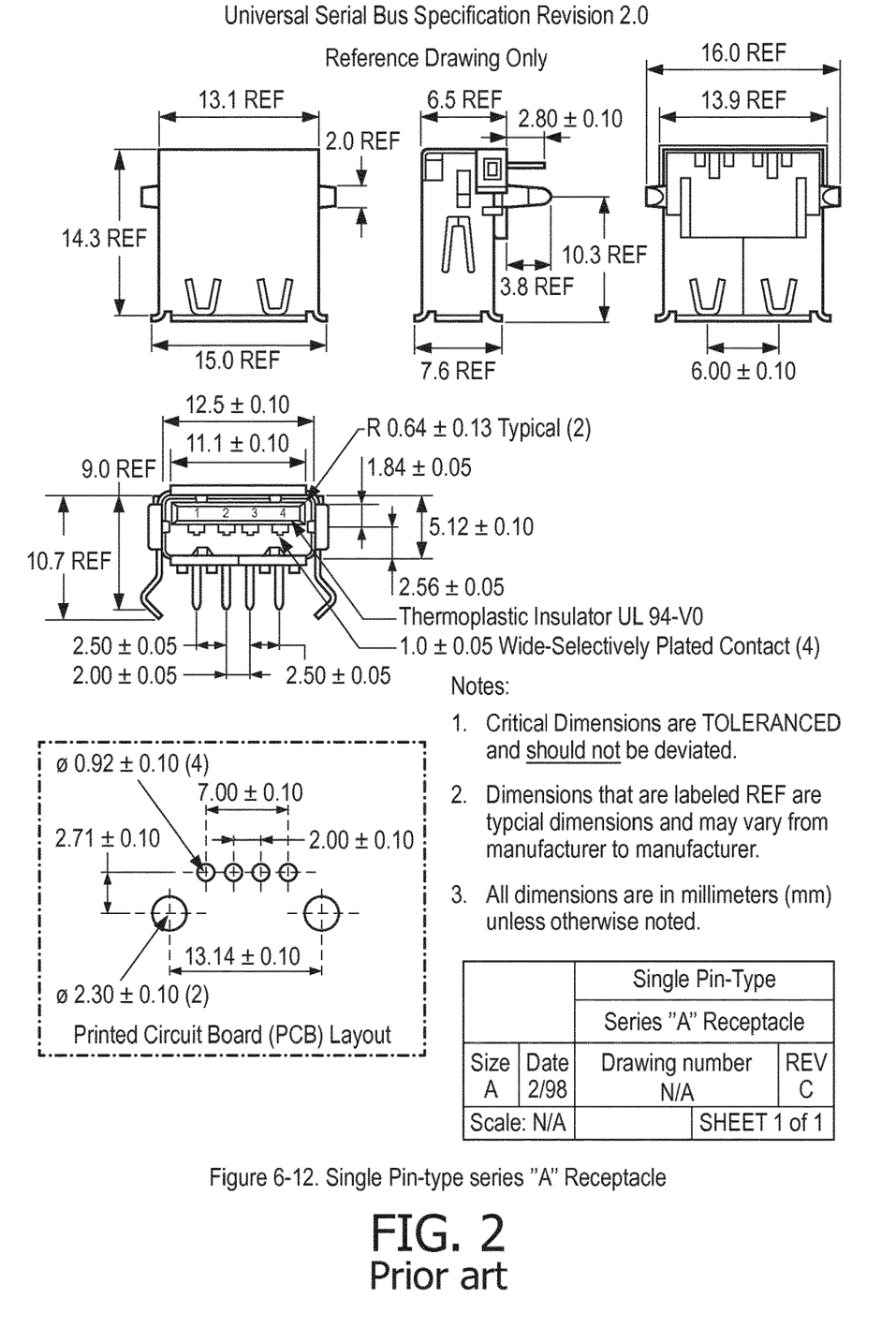
FIG. 2 illustrates a prior art USB Series A Receptacle according to Revision 2.0.

FIG. 2 illustrates a prior art USB Series A Receptacle according to Revision 2.0. The receptacle of FIG. 2 is described in more detail in document [1] and is adapted for being mated with the plug of FIG. 1. In particular a contact-bearing tongue of the receptacle in FIG. 2 is illustrated in the middle portion defines the USB Series A receptacle contact pad pitch specification, these contact pads having the same pitch as described above in relation to FIG. 1.

In the invention, in order to reduce component costs, a contact pad substrate conforming to the USB Series A receptacle contact pad pitch specification of FIG. 2 and FIG. 1 is used.

Figure 3:
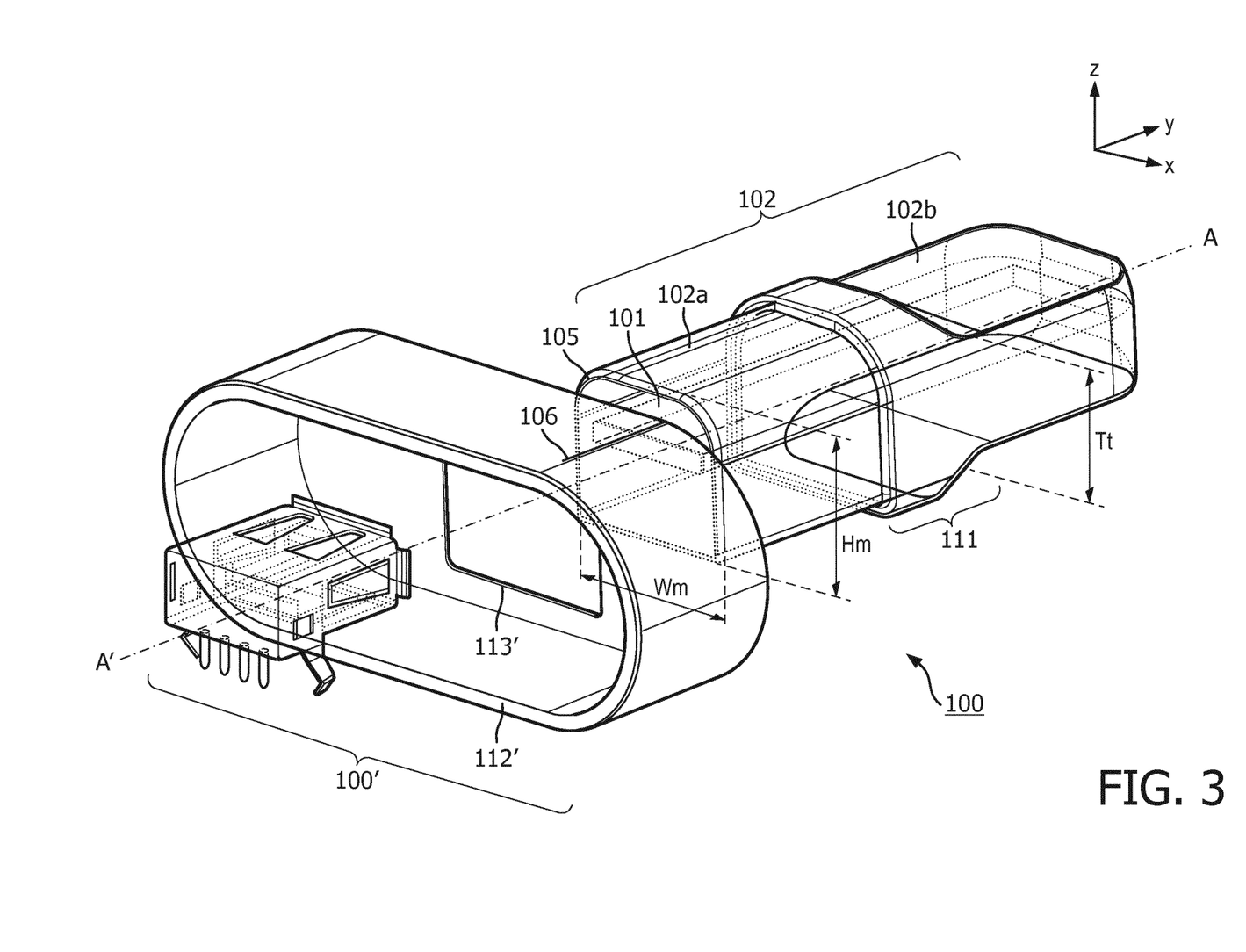
FIG. 3 illustrates a male connector 100 that includes a contact pad substrate 101 and a connector shell 102.
Figure 4:
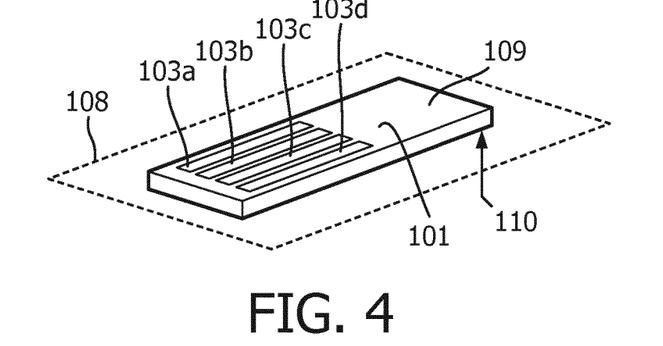
FIG. 4 illustrates a contact pad substrate 101 that includes a linear array of contact pads including two outermost contact pads 103a, 103d and two innermost contact pads 103b, 103c.
Figure 5:
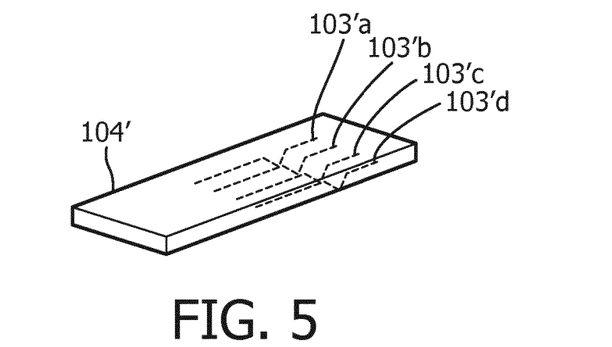
FIG. 5 illustrates a contact-bearing tongue 104' of a female connector 100' that includes contacts 103'a, 103'b, 103'c, 103'd.
Figure 6:
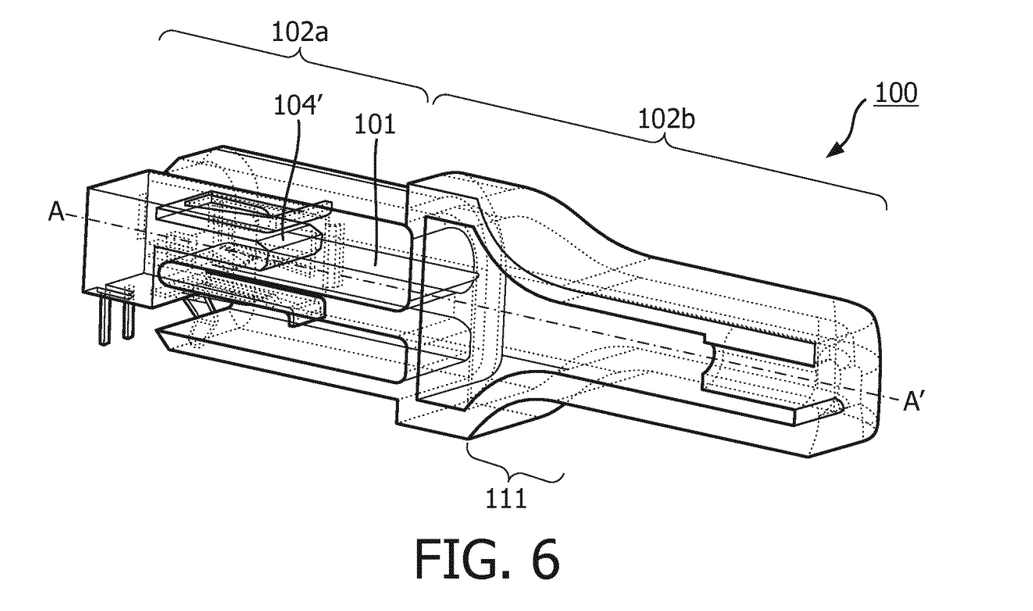
FIG. 6 illustrates a cross section through A-A' of the male connector illustrated in FIG. 1.

Thereto, FIG. 3 illustrates a male connector 100 that includes a contact pad substrate 101 and a connector shell 102. Male connector 100 is suitable for mating with exemplary corresponding female connector 100' in FIG. 3 by applying pressure along insertion axis A-A'. Contact pad substrate 101 is illustrated in more detail in FIG. 4, which illustrates a contact pad substrate 101 that includes a linear array of contact pads including two outermost contact pads 103a, 103d and two innermost contact pads 103b, 103c. Contact pad substrate 101 may include an insulator such as a polymer, fiberglass such as FR4, or a ceramic, and in some exemplary implementations may be a printed circuit board, PCB. The contact pads may be formed from any suitable conductor and may be a metal such as example gold, silver, aluminium and so forth. Moreover, the two outermost contact pads 103a, 103d in FIG. 3 and FIG. 4 are electrically connected together. This may be achieved using an electrical conductor (not shown). In some exemplary implementations this electrical conductor may be provided by an electrical trace within a PCB substrate. With reference to FIG. 3 and FIG. 4; in order to reduce component costs, the two innermost contact pads 103b, 103c have a pitch of 2.0 millimeters and the pitch between each innermost contact pad 103b, 103c and its nearest outermost contact pad 103a, 103d is 2.5 millimeters for aligning with corresponding contacts 103'a, 103'b, 103'c, 103'd of a contact-bearing tongue 104' of corresponding female connector 100' that conforms to a USB Series A receptacle contact pad pitch specification. FIG. 5 illustrates a contact-bearing tongue 104' of a female connector 100' that includes contacts 103'a, 103'b, 103'c, 103'd; and FIG. 6 illustrates a cross section through A-A' of the male connector illustrated in FIG. 1. Contact-bearing tongue 104' of FIG. 4 conforms to a USB Series A receptacle contact pad pitch specification and is dimensioned in order to fit within cavity 106 of male connector 100. It is to be noted that whilst a complete USB Series A receptacle is illustrated in FIG. 3 and FIG. 5 as an exemplary corresponding female connector 100', only contact-bearing tongue 104' illustrated in FIG. 5 and FIG. 6 from this complete USB Series A receptacle is required in corresponding female connector 100' in order to make contact with contact pad substrate 101. Thus male connector 100 may be connected to other geometries of female connectors 100' having at least a suitable contact-bearing tongue 104'.

With further reference to FIG. 3 and FIG. 4, connector shell 102 is formed from an insulating material and comprises a tubular portion 102a for insertion into the corresponding female connector 100', and a handling portion 102b for handling during insertion. Various insulators are contemplated for use as connector shell 102, including without limitation polymers such as Polyethylene terephthalate, PET, high density polyethylene, HDPE, low density polyethylene, LDPE, polypropylene, PP, or polycarbonate; or fiberglass. Connector shell 102 may be formed as a unitary body or be provided by separate parts in order to e.g. facilitate the incorporation of contact pad substrate 101 therein.

Tubular portion 102a includes end face 105 that has an opening that defines an entrance to cavity 106. Cavity 106 extends along the insertion axis A-A' in order to receive within the tubular portion 102a the contact-bearing tongue 104' of the corresponding female connector 100'. Cavity 106 may thus be sufficiently wide, high, and/or deep in order to receive contact-bearing tongue 104'. In some applications a cavity width in the range 8-15 millimeters is contemplated. In another exemplary application a cavity width of 11.1±0.1 millimeters is contemplated in order to allow for the reception of an existing tongue portion of a Series A receptacle illustrated in FIG. 2. In another exemplary application a cavity width of 11.9±0.1 millimeters is contemplated in order to do likewise, and allow for some additional insertion space. The use of an existing tongue portion may, as with the use of an existing contact substrate 101, provide a further cost reduction. In some applications a cavity height in the range 1-5 millimeters is contemplated. In one exemplary application a cavity height of 2.85±0.1 millimeters is contemplated. In some applications a cavity length in the range 10-20 millimeters is contemplated. In one exemplary application a cavity length of 14.65±0.1 millimeters is contemplated.

As also illustrated in FIG. 3, contact pad substrate 101 is disposed within cavity 106 such that the contact pads 103a, 103b, 103c, 103d of the linear array are distributed transversely with respect to end face 105, and such that the contact pads are exposed within the cavity 106 for making electrical contact with the corresponding contacts 103'a, 103'b, 103'c, 103'd of contact-bearing tongue 104' of female connector 100' when the male connector 100 is mated with the female connector 100'.

As mentioned above, male connector 100 is contemplated for use in the vicinity of electrical equipment such as a computer or a tablet in which electrical connectors such as USB Series A receptacles are available. However, male connector 100 is contemplated for use in applications in which the power supply of a conventional USB 2 connector or pitch-compatible USB 3 connector, i.e. the nominal +5 Volts and 0 Volts that is conventionally applied across the two outermost contact pads 103a 103d, is not required. Thus, in the male connector the two outermost contact pads 103a, 103d, are electrically connected together. This ensures that, despite the contact pad pitch specification of male connector 100 conforming to that of the USB Series A receptacle contact pad pitch specification, even if contact pad substrate 101 were inserted into such a receptacle, no potential difference can be applied between contact pads 100a, 100d. In the contemplated medical applications in which the male connector may be used, applying even moderate external potential differences such as this to e.g. parts of a patient's nervous system, can have harmful effects.

Moreover, tubular portion 102a of connector shell 102 that is adapted for insertion into corresponding female connector 100' is formed from an insulating material. Conventionally, the corresponding insertable body of a USB 2 Series A plug is formed from a conductor in order to electrically shield the contacts disposed therein from EMI. This conductor also serves to make electrical contact with the corresponding electrical shield of the corresponding USB 2 Series A receptacle. As mentioned above, male connector 100 is however contemplated for use in the vicinity of electrical equipment such as a computer or a tablet in which other electrical connectors such as USB Series A receptacles are available. However, in particular when such electrical equipment is un-grounded, the electrical shield of this receptacle can float to a high voltage of many tens of volts or more above ground potential. By forming tubular portion 102a from an insulating material, it is therefore ensured that even if end face 105 were temporarily touched onto the electrical shield of a USB 2 Series A receptacle, the floating potential of the electrical equipment cannot be applied to a patient. Thus, in combination with the feature of electrically shorting together the two outermost contact pads 103a, 103d, this feature further reduces the risk of applying a harmful potential to a patient through mis-insertion of the male connector into known female connectors such as a USB Series A receptacle that may have a similar appearance.

Figure 7:
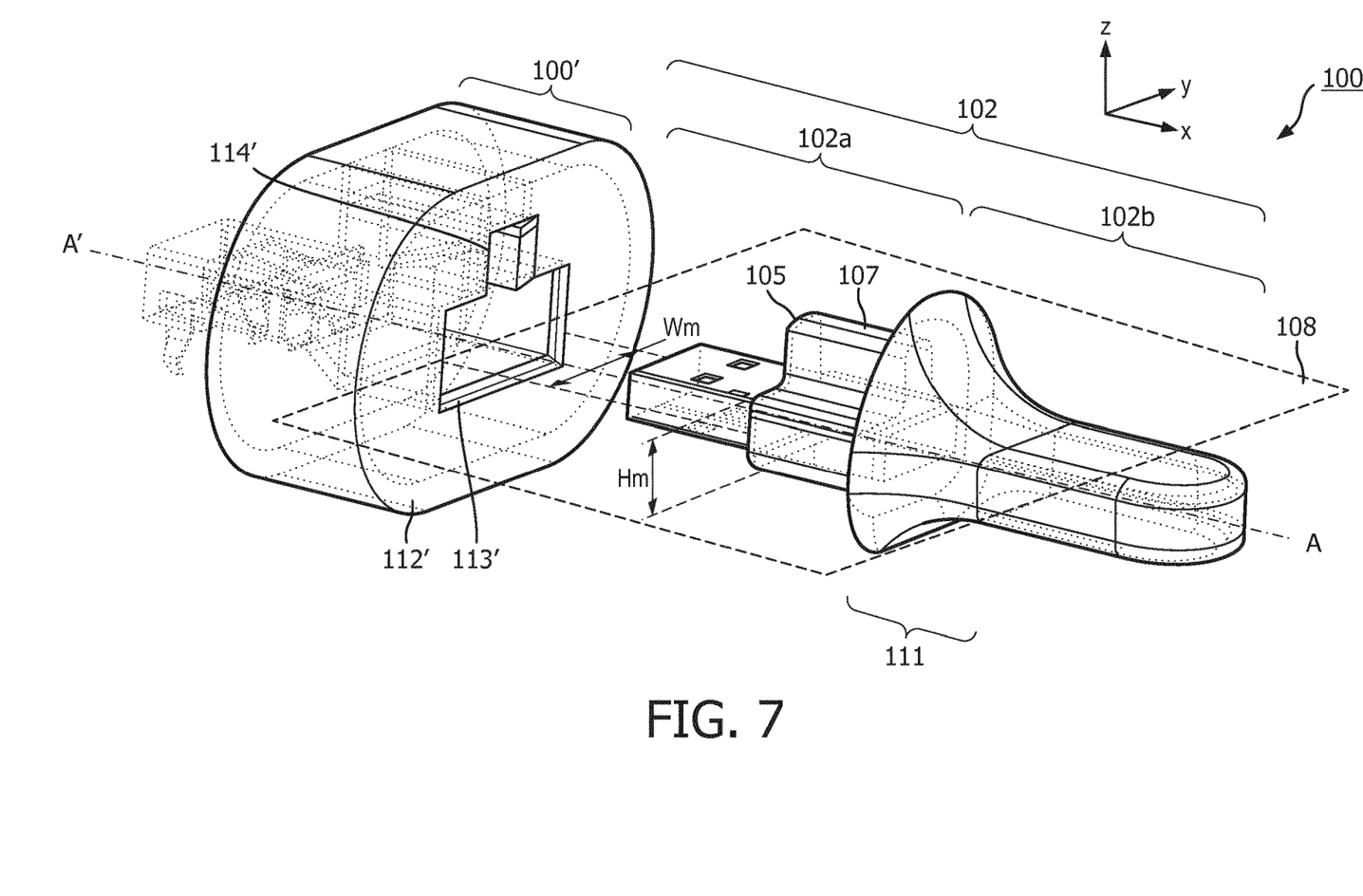
FIG. 7 illustrates a male connector 100 that includes a connector shell 102 having a tubular portion 102a that includes a first embodiment of an insertion key 107.

In one implementation, male connector 100 may include an insertion key in order to prevent insertion of tubular portion 102a into a USB Series A receptacle. In general, tubular portion 102a of male connector 100 in FIG. 3 may adapted in order to include an insertion key 107 that extends along insertion axis A-A' and outwards with respect to the cavity 106 for preventing insertion of the tubular portion 102a into a USB Series A receptacle. In this respect, with reference to FIG. 3. FIG. 4 and FIG. 7, contact pad substrate 101 may lie in substrate plane 108a. End face 105 may have a height between an outermost surface of insertion key 107 and an opposing outer surface of tubular portion 102a exceeding 4.6 millimeters in a normal direction with respect to substrate plane 108a. Likewise end face 105 may have a width between an outermost surface of insertion key 107 and an opposing outer surface of tubular portion 102a exceeding 12.1 millimeters in a direction parallel to substrate plane 108a. The specified dimensions lie outside those of a USB Series A plug, which prescribes an insertable body having a maximum width of 12.00±0.1 millimeters, and a maximum height of 4.5±0.1 millimeters. In the same manner, in another implementation the aforementioned height may exceed 5 millimeters and the aforementioned width may exceed 13 millimeters.

Consequently, whilst forming tubular portion 102a of connector shell 102 from an insulating material reduces the risk of applying a harmful potential to a patient from even touching end face 105 onto an incorrect female connector, insertion key 107 further reduces this risk by preventing the actual insertion of male connector 100 into a USB Series A receptacle. Moreover, in combination with the feature of electrically shorting together the two outermost contact pads 103a, 103d together, insertion key 107 has the synergistic effect of preventing damage to the electrical equipment that might otherwise result from the mis-insertion of male connector 100 into a USB Series A receptacle.

Thereto, FIG. 7 illustrates a male connector 100 that includes a connector shell 102 having a tubular portion 102a that includes a first embodiment of an insertion key 107. Whilst in male connector 100 in FIG. 7, contact pad substrate 101 not disposed within cavity 106, FIG. 7 is provided in order to illustrate an insertion key 107 that may be incorporated into tubular portion 102a in FIG. 3 by extending tubular portion 102a in FIG. 3 in the +z-direction as illustrated in FIG. 7. When applied to FIG. 3, insertion key 107 of FIG. 7 may thus extend in the z-direction and occupy a portion of the entire insertion length of tubular portion 102a, as illustrated in FIG. 7. Alternatively, insertion key 107 of FIG. 7 may extend in the +z-direction and occupy the entire insertion length of tubular portion 102a. Insertion key 107 may alternatively extend beyond the end face 105 of tubular portion 102a in FIG. 3.

Figure 8:
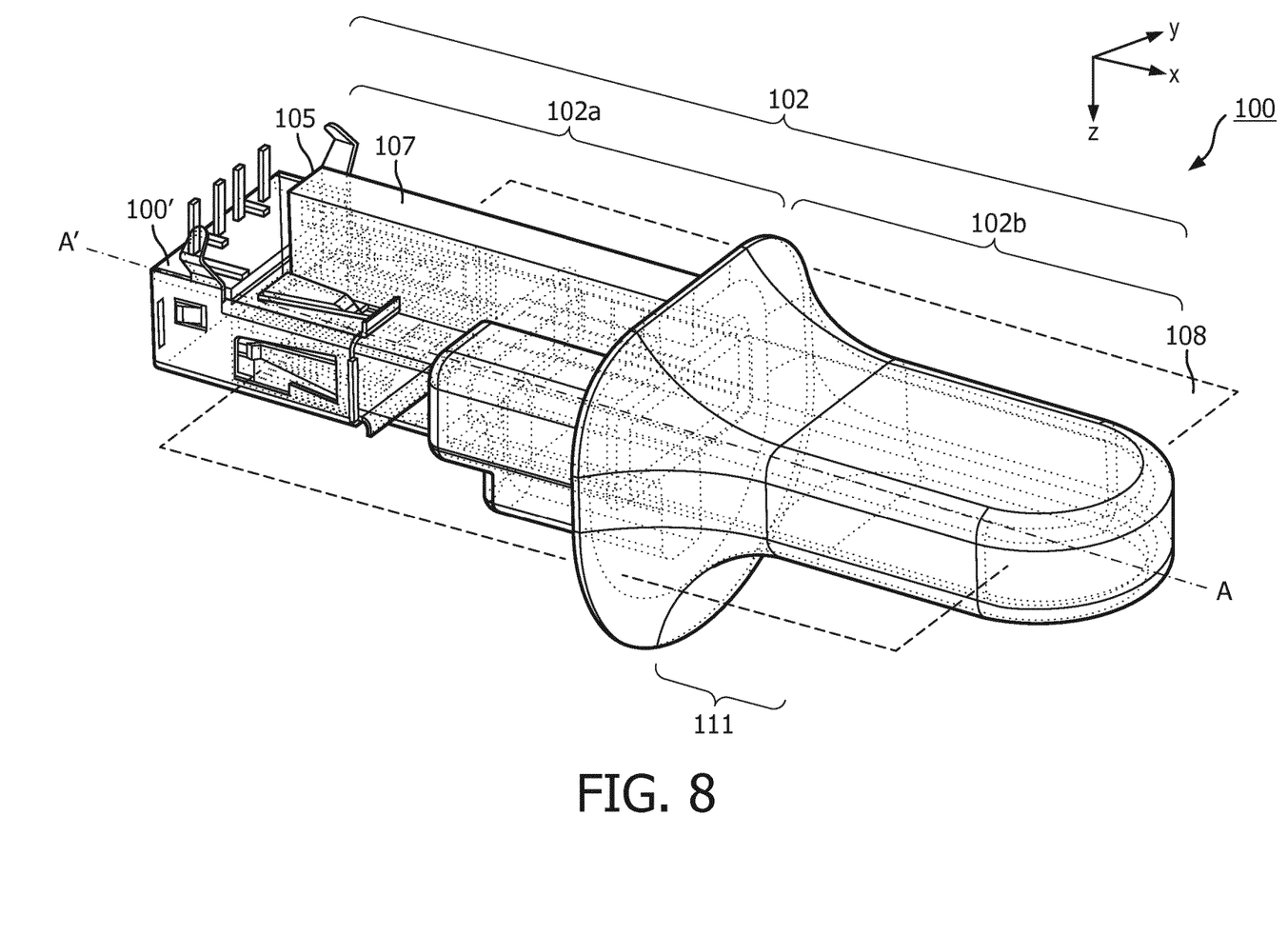
FIG. 8 illustrates a male connector 100 that includes a connector shell 102 having a tubular portion 102a that includes a second embodiment of an insertion key 107.
Figure 9:
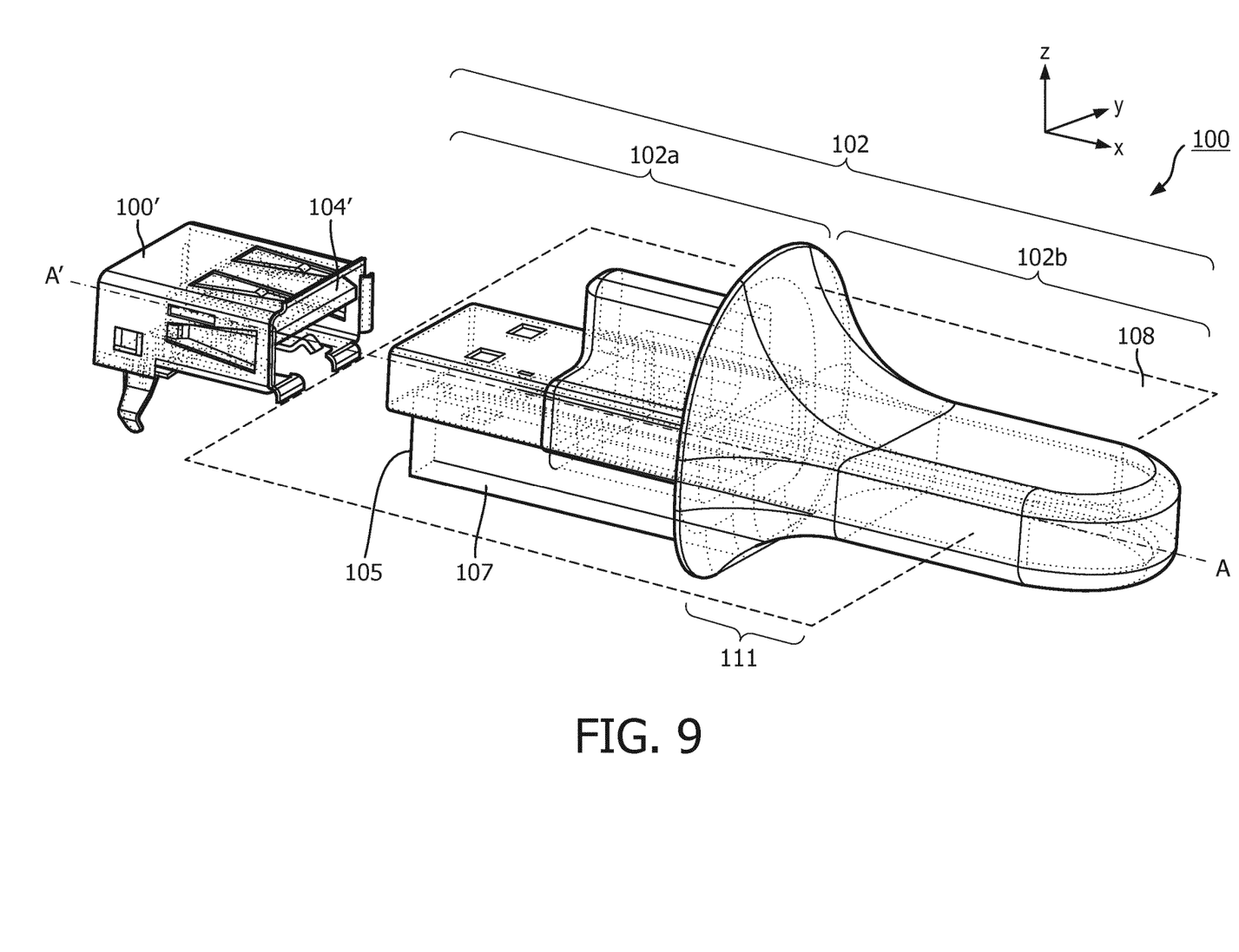
FIG. 9 illustrates an inverted version of the male connector illustrated in FIG. 8.

FIG. 8 illustrates a male connector 100 that includes a connector shell 102 having a tubular portion 102a that includes a second embodiment of an insertion key 107. As with FIG. 7, whilst in male connector 100 in FIG. 8, contact pad substrate 101 not disposed within cavity 106, FIG. 8 is provided in order to illustrate another insertion key 107 that may be incorporated into tubular portion 102a in FIG. 3 by extending tubular portion 102a in FIG. 3. In contrast to FIG. 7, insertion key 107 in FIG. 8 extends in the −z direction and occupies the entire insertion length of tubular portion 102a. When applied to FIG. 3, insertion key 107 of FIG. 8 may thus extend in the −z-direction and occupy the entire insertion length of tubular portion 102a, as illustrated in FIG. 8. Alternatively, insertion key 107 of FIG. 8 may extend in the +z-direction and/or occupy a portion of entire insertion length of tubular portion 102a. Insertion key 107 may alternatively extend beyond the end face 105 of tubular portion 102a in FIG. 3. FIG. 9 illustrates an inverted version of the male connector illustrated in FIG. 8.

Thus, with reference to FIG. 3 and FIG. 4, in which contact pad substrate 101 lies in a substrate plane 108; insertion key 107 may optionally extend normally outwards with respect to the substrate plane 108.

With continued reference to FIG. 3 and FIG. 4, in which contact pad substrate 101 includes first surface 109 and second surface 110 and in which contact pads 103a, 103b, 103c, 103d are disposed on first surface 109; insertion key 107 may optionally extend normally outwards with respect to first surface 109.

In some exemplary implementations a maximum width or a maximum height of end face 105 of tubular portion 102a of male connector 100 may optionally be sized in order to prevent insertion of the tubular portion 102a into a USB Series A receptacle. This further reduces the risk of mis-insertion of the male connector, and consequently the risk of harm to a patient or damage to electrical equipment connected thereto. Thus with reference to FIG. 3 and to FIG. 7, optionally, i) a maximum width Wm of end face 105 of tubular portion 102a parallel to the linear array is greater than 12.1 millimeters and/or ii) a maximum height Hm of end face 105 of tubular portion 102a perpendicular to the linear array is greater than 4.6 millimeters, for preventing insertion of the tubular portion 102a into a USB Series A receptacle. In embodiments that include insertion key 107, these dimensions may include insertion key 107. The specified dimensions lie outside those of a USB Series A plug, which prescribes an insertable body having a maximum width of 12.00±0.1 millimeters, and a maximum height of 4.5±0.1 millimeters. In the same manner, in a preferred implementation, i) a maximum width Wm of tubular portion 102a parallel to the linear array may be greater than 13 millimeters and/or ii) a maximum height Hm of the tubular portion 102a perpendicular to the linear array may be greater than 5 millimeters. In one exemplary application i) a width Wm of tubular portion 102a parallel to the linear array may be 13.5 millimeters±0.1 millimeters and/or ii) a height Hm of the tubular portion 102a perpendicular to the linear array may be 7.5 millimeters±0.1 millimeters. An exemplary length of tubular portion 102a may be 14.65 millimeters±0.1 millimeters.

In some exemplary implementations an outer cross section of the tubular portion 102a in a plane that is normal to insertion axis A-A' may have curved or chamfered corners. This may facilitate easier insertion of male connector 100.

In some exemplary implementations handling portion 102b of connector 100 may optionally include tapered region 111 having a taper thickness Tt perpendicular to the linear array, wherein taper thickness Tt increases towards tubular portion 102a for preventing a finger of a user from slipping towards tubular portion 102a during mating of male connector 100 with corresponding female connector 100'. Such a tapered region 111 is illustrated in FIG. 3, and in FIG. 6, and tapered regions 111 illustrated in FIG. 7, FIG. 8 and FIG. 9 may likewise be incorporated into male 100 connector of FIG. 3. Tapered region 111 may be disposed on one or both sides of substrate plane 108. In some exemplary implementations the maximum taper thickness Tt may exceed 9 millimeters. In one implementation the maximum taper thickness is 10 millimeters.

As mentioned above, in the contemplated medical applications in which the male connector may be used, sterility is a key requirement. Whilst male connector 100, together with any medical device connected thereto, is typically sterilized and packaged before use in order to maintain that sterility, a console to which the male connector is connected by way of a corresponding female connector 100', may be sterilized less often. Tapered region 111 reduces the risk that the sterile finger of a user that handles the male connector slips and contacts the less-sterile console, and subsequently transfers any harmful substances thereon to a patient by way of the user's finger.

In one implementation, male connector 100 illustrated in FIG. 3 may further include a sensor and an electrical cable, not illustrated. The sensor may be any type of sensor that converts a physical parameter into an electrical signal, including but not limited to an ultrasound sensor a temperature sensor, an optical sensor, a pair of electrodes, a radiation sensor or an audio sensor. In this implementation the sensor comprises a first electrical contact and a second electrical contact. The electrical cable comprises a first signal conductor, a second signal conductor and an electrical shield configured to electrically shield the first signal conductor and the second signal conductor. The first electrical contact of the sensor is electrically connected to one of the two innermost contact pads $103b$, $103c$ of male connector 100 by the first signal conductor, and the second electrical contact of the sensor is electrically connected to the other of the two innermost contact pads $103b$, $103c$ of male connector 100 by the second signal conductor. The electrical shield is electrically connected to both of the two outermost contact pads $103a$, $103d$ of the contact pad substrate. The sensor may optionally be attached to a medical device, such as, without limitation a needle, catheter, a guidewire, a biopsy device, a guidewire, a pacemaker lead, an intravenous line or a surgical tool in general.

As mentioned above, in so doing, a single electrical shield may shield both signal conductors. The use of only three electrical conductors, including the shield, in the electrical cable improves its flexibility thereby making it easier to deploy the sensor. In known USB male connectors up to five electrical conductors, including the shield, are used in such an electrical cable: two for electrical signals, two for the nominal +5 Volts and 0 Volts power supply, and one for the electrical shield.

A female connector 100' for mating with male connector 100 may also be provided. Optionally male connector 100 and female connector 100' may be connected together as an assembly. With reference to FIG. 3, FIG. 5 and FIG. 7, female connector 100' includes housing 112' comprising housing opening 113' for receiving tubular portion $102a$ of connector shell 102 of male connector 100. Housing opening 113' includes notch 114' that is configured to receive insertion key 107. Female connector 100' also includes contact-bearing tongue 104' for insertion into cavity 106 of male connector 100. Contact-bearing tongue may thus have a width, a height and/or a length configured to fit into cavity 106. Contact-bearing tongue 104' comprises a linear array of contacts $103'a$, $103'b$, $103'c$, $103'd$ including two inner sprung contacts $103'b$, $103'c$ and two outer sprung contacts $103'a$, $103'd$ arranged respectively for making electrical contact with the two innermost contact pads $103b$, $103c$ and the two outermost contact pads $103a$, $103d$ of male connector 100.

Contact-bearing tongue 104' may for example be formed from one of the materials described in relation to contact pad substrate 101 or connector shell 102. Various types of known sprung contacts may be used, the spring of which acts to improve electrical contact with the corresponding contact pads on contact pad substrate 101.

In summary, a male connector that includes a contact pad substrate and a connector shell has been described. The contact pad substrate includes a linear array of contact pads that are adapted for aligning with corresponding contacts of a contact-bearing tongue of a corresponding female connector that conforms to a USB Series A receptacle contact pad pitch specification. The two outermost contact pads of the linear array are electrically connected together. The connector shell is formed from an insulating material and comprises a tubular portion for insertion into the corresponding female connector, and a handling portion for handling during insertion.

Various embodiments, implementations and options have been described in relation to a male connector, and it is noted that these may be combined to achieve further advantageous effects.

As used herein, the term "or" should be interpreted as a disjunctive "or." Further, the term "or" and the term "and" when prefaced by the term "at least one of" or the term "one or more of" should be interpreted as a disjunctive list such that, for example, a list of "at least one of A or B" or a list of "one or more of A and B" or a list of "A or B" should be interpreted to include either A or B, one of A and one of B, a combination of one or more of each of A and B; both A and B; or combinations of one or more of A and one or more of B, and such other combinations as relevant to the recited list or terms consistent with the corresponding description in the specification.

The invention claimed is:

1. A male connector for mating with a corresponding female connector by applying pressure along an insertion axis, the male connector comprising:
    a contact pad substrate; and
    a connector shell;
    wherein the contact pad substrate comprises a linear array of contact pads including two outermost contact pads and two innermost contact pads, the two outermost contact pads being electrically connected together,
    wherein the two innermost contact pads have a pitch of substantially 2.0 millimeters and a pitch between each innermost contact pad and its nearest outermost contact pad is substantially 2.5 millimeters for aligning with corresponding contacts of a contact-bearing tongue of the corresponding female connector that conforms to a USB Series A receptacle contact pad pitch specification,
    wherein the connector shell is formed from an insulating material and comprises a tubular portion for insertion into the corresponding female connector, and a handling portion for handling during insertion,
    wherein the tubular portion includes an end face having an opening that defines an entrance to a cavity, which cavity extends along the insertion axis for receiving within the tubular portion the contact-bearing tongue of the corresponding female connector, wherein the contact pad substrate is disposed within the cavity such that the contact pads of the linear array are distributed transversely with respect to the end face, and such that the contact pads are exposed within the cavity for making electrical contact with the corresponding contacts of the contact-bearing tongue of the corresponding female connector when the male connector is mated with the corresponding female connector.

2. The male connector according to claim 1, wherein the tubular portion comprises an insertion key that extends along the insertion axis and outwards with respect to the cavity for preventing insertion of the tubular portion into a USB Series A receptacle.

3. The male connector according to claim 2, wherein the contact pad substrate lies in a substrate plane and wherein the insertion key extends normally outwards with respect to the substrate plane.

4. The male connector according to claim 3, wherein the contact pad substrate further comprises a first surface and a second surface, the contact pads being disposed on the first surface, and wherein the insertion key extends normally outwards with respect to the first surface.

5. The male connector according to claim 1, wherein a maximum width of the end face of the tubular portion parallel to the linear array is greater than 12.1 millimeters or ii) wherein a maximum height of the end face of the tubular portion perpendicular to the linear array is greater than 4.6 millimeters, for preventing insertion of the tubular portion into a USB Series A receptacle.

6. The male connector according to claim 1, wherein an outer cross section of the tubular portion in a plane that is normal to the insertion axis has curved or chamfered corners.

7. The male connector according to claim 1, wherein the handling portion further comprises a tapered region having a taper thickness perpendicular to the linear array, wherein the taper thickness increases towards the tubular portion for preventing a finger of a user from slipping towards the tubular portion during mating of the male connector with the corresponding female connector.

8. The male connector according to claim 1, further comprising a sensor and an electrical cable,
  wherein the sensor comprises a first electrical contact and a second electrical contact,
  wherein the electrical cable comprises a first signal conductor, a second signal conductor and an electrical shield configured to electrically shield the first signal conductor and the second signal conductor,
  wherein the first electrical contact of the sensor is electrically connected to one of the two innermost contact pads of the male connector by the first signal conductor, and wherein the second electrical contact of the sensor is electrically connected to the other of the two innermost contact pads of the male connector by the second signal conductor, and
  wherein the electrical shield is electrically connected to both of the two outermost contact pads of the contact pad substrate.

9. A medical device comprising the male connector according to claim 8, wherein the sensor is attached to the medical device.

10. An apparatus comprising the male connector according to claim 1 and the corresponding female connector, wherein the corresponding female connector comprises:
  a housing comprising a housing opening for receiving the tubular portion of the connector shell of the male connector, the housing opening including a notch configured to receive an insertion key; and
  a contact-bearing tongue for insertion into the cavity of the male connector;
  wherein the contact-bearing tongue comprises a linear array of contacts including two inner sprung contacts and two outer sprung contacts arranged respectively for making electrical contact with the two innermost contact pads and the two outermost contact pads of the male connector.

* * * * *